United States Patent
Watson

Patent Number: 6,000,279
Date of Patent: Dec. 14, 1999

[54] RUBBER TESTING

[76] Inventor: William Ferguson Watson, 43 Castle Avenue, Hyth, Kent CT21 5HD, United Kingdom

[21] Appl. No.: 09/043,018
[22] PCT Filed: Sep. 6, 1996
[86] PCT No.: PCT/GB96/02201
  § 371 Date: Mar. 4, 1998
  § 102(e) Date: Mar. 4, 1998
[87] PCT Pub. No.: WO97/09602
  PCT Pub. Date: Mar. 13, 1997

[30] Foreign Application Priority Data

Sep. 6, 1995 [GB] United Kingdom .................. 9518176

[51] Int. Cl.$^6$ .................................................. G01N 11/14
[52] U.S. Cl. .................................. 73/54.39; 73/843
[58] Field of Search ................................ 73/54.39, 843, 73/54.23, 54.33

[56] References Cited

U.S. PATENT DOCUMENTS

| | | | |
|---|---|---|---|
| 3,479,858 | 11/1969 | Umeno et al. | 73/843 X |
| 4,092,849 | 6/1978 | Maxwell | 73/843 X |
| 4,275,600 | 6/1981 | Turner et al. . | |
| 4,352,287 | 10/1982 | Orth et al. . | |
| 4,566,324 | 1/1986 | Vinogradov et al. . | |
| 4,601,195 | 7/1986 | Garritano . | |
| 4,760,734 | 8/1988 | Maxwell | 73/843 |

FOREIGN PATENT DOCUMENTS

| | | | |
|---|---|---|---|
| 0 107 593 | 5/1984 | European Pat. Off. . | |
| 0 132 056 | 1/1985 | European Pat. Off. . | |
| 0 449 586 | 10/1991 | European Pat. Off. . | |
| 873976 | 7/1942 | France | 73/54.39 |
| 764850 | 1/1957 | United Kingdom . | |
| 1 365 677 | 9/1974 | United Kingdom . | |
| WO 85/03128 | 7/1985 | WIPO . | |

*Primary Examiner*—Daniel S. Larkin
*Attorney, Agent, or Firm*—Davis and Bujold

[57] ABSTRACT

A test sample of raw or compounded rubber is squeezed from a loading chamber (7) through selectively-aligned passages (8,12) to fill an annular space (1) between a coaxial stator (5) and rotor (4). Measurements of viscous torque are provided by a sensor (15), and a load cell (14) provides measurements of the force exerted axially by the sample. The torque and axial-force measurements are plotted against time (16 FIG. 4, 17 FIG. 5) as representative respectively of the viscosity V and elasticity of recovery E of the sample, and are compared for correspondence (within limits 19, 20) with earlier-plotted characteristics of an acceptable rubber for processing. Temperature of the sample is regulated by a heater (18) and rotation of the rotor (4) is at a speed and for a duration corresponding to that of the next processing stage.

16 Claims, 3 Drawing Sheets

RUBBER TESTING

This invention relates to methods of testing rubber and apparatus for carrying out such methods.

One of the most, if not the most, significant factors affecting quality and consistency in manufacture of rubber products, is the quality of the raw rubber used. However, the quality and consistency of raw rubber, particularly natural rubber but also to a lesser extent synthetic rubbers, varies considerably. It is accordingly desirable to have a method of testing rubber-quality that can be readily applied before or during the early stages of the manufacturing process, towards achieving assurance of consistency of manufactured product. It is one of the objects of the present invention to provide such a method and also an apparatus for carrying out the method.

According to one aspect of the present invention, there is provided a method of testing rubber wherein a sample of the rubber is entered to fill an annular space defined between coaxial cylindrical surfaces of two relatively-rotatable members, and measurements of the viscous torque of the sample and the force it exerts axially of the annular space during relative rotation of the two members is derived to provide a measure of quality of the sample.

It has been found that the measurements of torque and axially-exerted force of the sample can be used with advantage for assessing the quality of the rubber in relation to its acceptability or otherwise for consistency of manufactured product. In the manufacture of tyres, for example, it is necessary to have reproducibility of properties such as tensile strength and resistance to wear, and the method of the invention has been found to enable criteria of acceptability or suitability for the starting material, whether in the raw or compounded condition, to be established.

A multiplicity of measurements of the viscous torque and the axial force may be derived during a period of relative rotation of the two members so as to provide time-related characteristics dependent, respectively, upon the viscosity and the elasticity of recovery of the sample. Determination of acceptability or otherwise of the sample may then be made in dependence upon the degree of conformity of the characteristics to predetermined criteria.

The measurements may be made for each of a series of samples taken at successive stages of manufacture of a rubber product. For example, the samples may be taken from the raw rubber, from the product of compounding in a primary masticator-mixer, and from the product of extrusion, calendering, or injection-moulding of the compounded rubber.

The method of testing is desirably carried out at a temperature and for a duration comparable with the temperature and duration of the next processing stage to which the rubber from which the sample was taken, is to be submitted. The temperature in primary compounding is generally in the range 130 to 150 degrees Celsius for natural rubber, 140 to 170 degrees Celsius for general-purpose synthetic rubbers, and 100 to 120 degrees Celsius for butyl rubbers, and may exceed 200 degrees Celsius for high temperature rubbers. Moreover, the speed of relative rotation of the two members is desirably such as to give rise to a rate of shear within the sample comparable with that to which the rubber is to be submitted in the next processing stage. The speed of relative rotation of the two members may in this respect be within the range 50 to 1,000 revolutions per minute, or more especially within the range 100 to 500 revolutions per minute.

According to another aspect of the present invention, an apparatus for testing a sample of rubber comprises two relatively-rotatable members having coaxial cylindrical surfaces to define an annular space between the two members for receiving the sample, means for rotating the two members relative to one another, means to derive a measurement dependent upon the viscous torque of the sample, and means to derive a measurement dependent upon the force exerted axially of the annular space during relative rotation of the two members.

The apparatus may include means for heating the sample within the annular space, and the axial length of the annular space may be substantially larger than its radial width to minimize end effects.

Also, the apparatus may include means for blocking one end of the annular space during relative rotation of the two members, and in these circumstances the means for deriving a measurement dependent upon axial force may be responsive to the force exerted axially by the sample, at the other end of the space. A loading chamber for receiving the sample of rubber may be coupled to the annular space via a plurality of passages that open axially into said one end of the space. Ram means may then be provided for forcing the sample from the loading chamber into the annular space via these passages.

A method of testing rubber, and an apparatus for use in the method, will now be described, by way of example, with reference to the accompanying drawings, in which.

Figure 1:
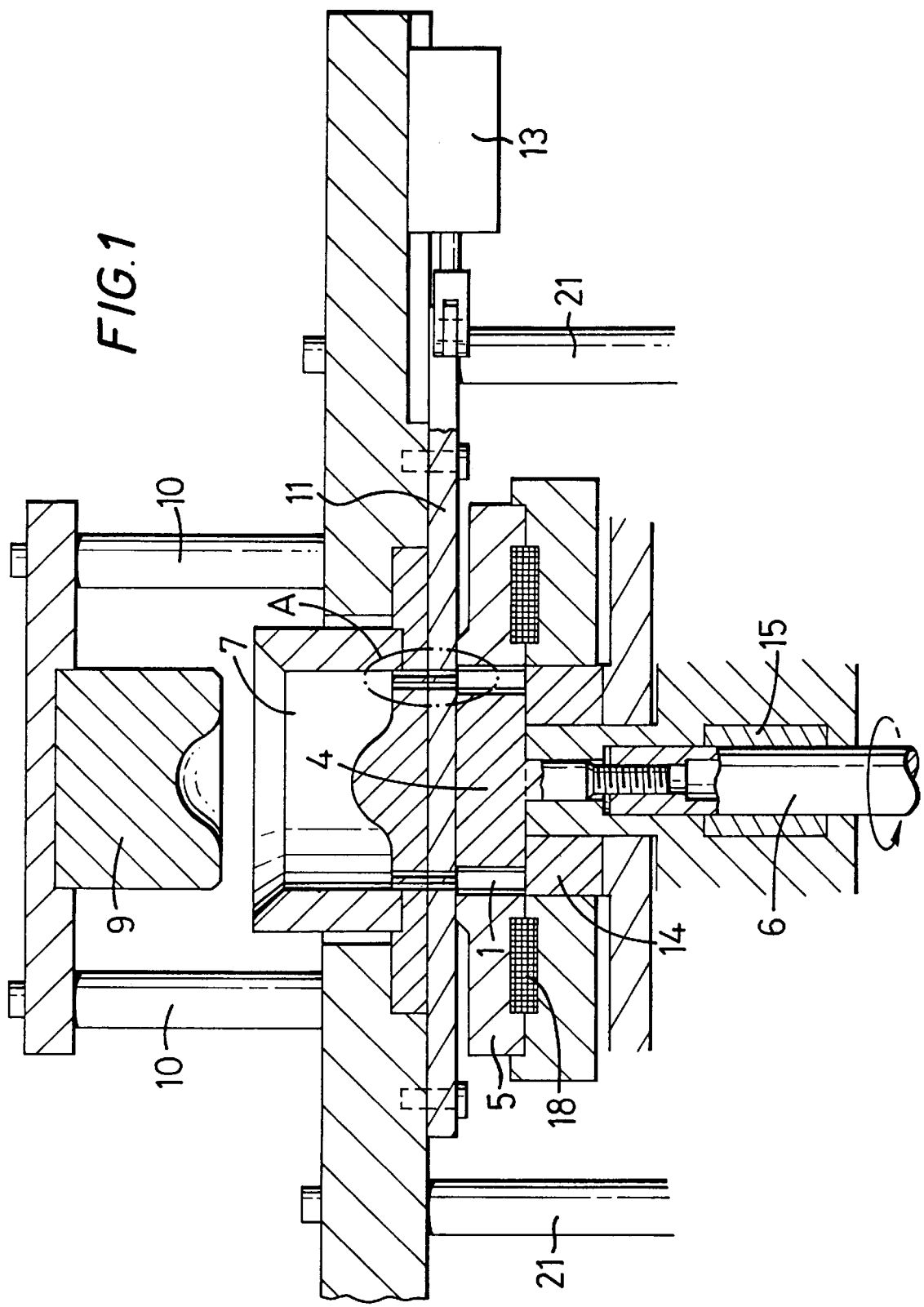
FIG. 1 is a sectional side elevation of part of the rubber-testing apparatus according to the invention.
Figure 2:
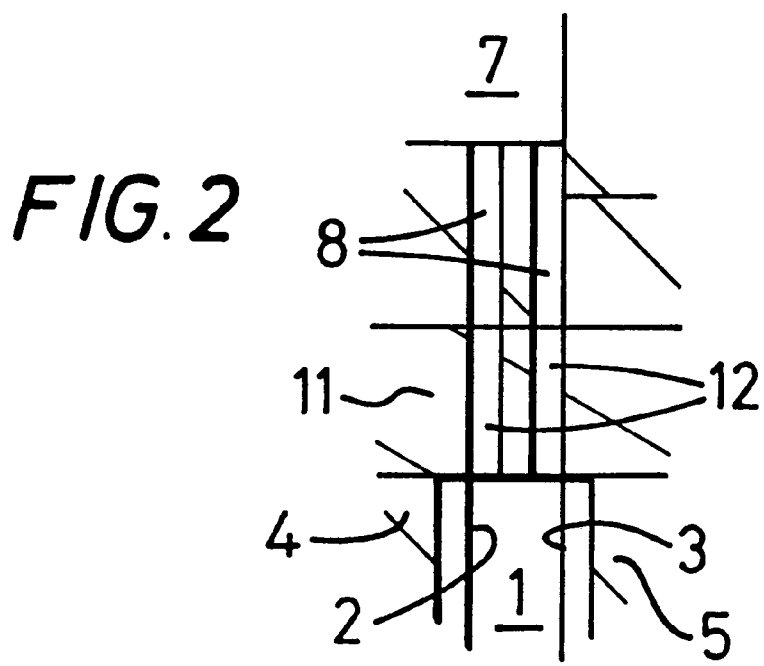
FIGS. 2 and 3 are enlarged views of the region designated A in FIG. 1 during different stages of the rubber-testing method of the invention.

Referring to FIGS. 1 and 2, the rubber-testing apparatus involves an annular space 1 for receiving the sample of rubber to be tested. The space 1 is defined between coaxial cylindrical surfaces 2 and 3 respectively of a rotor 4 and stator 5. The rotor 4 is mounted on a shaft 6 for rotation relative to the stator 5 by a motor (not shown), and the sample is entered into the space 1 from a loading chamber 7.

Figure 3:
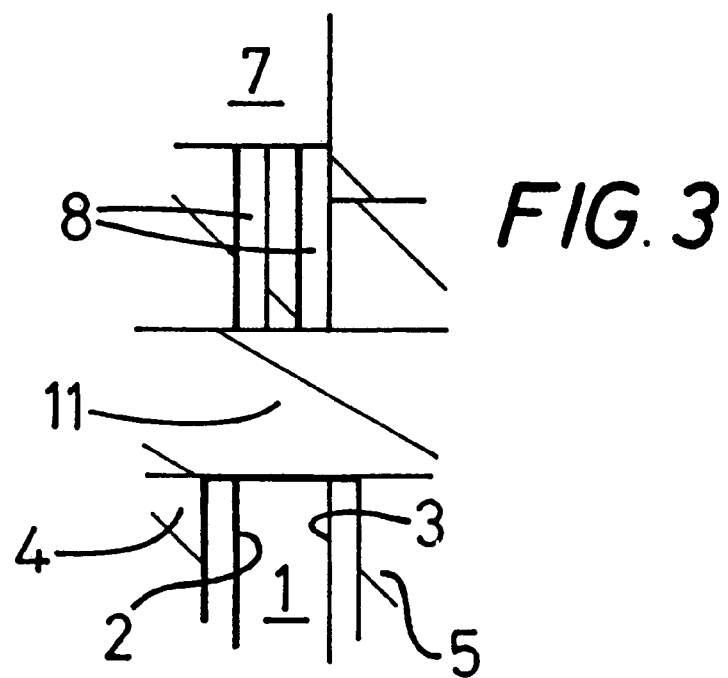

Sample rubber is loaded into the chamber 7 and passes down into the space 1 via two concentric rings of passages 8 that open through the bottom of the chamber 7. More particularly, a ram 9 that is carried by rods 10 is operated to squeeze the sample rubber downwardly into the passages 8. A movably-mounted plate 11, which is carried with the chamber 7 to extend across the top of the annular space 1, has passages 12 therethrough that (as illustrated in FIGS. 1 and 2) align with the passages 8 to allow the rubber to enter the space 1. The plate 11 is slidable under control of a motor 13 to move the passages 12 out of alignment with the passages 8 as illustrated in FIG. 3. This enables the top of the space 1 to be completely closed off when it is full.

The bottom of the space 1 is closed by an annular load cell 14 which provides an electrical signal in accordance with the force exerted by the sample axially of the space 1. The measurements represented by this signal are plotted against time during rotation of the rotor 4, as also are measurements represented by an electric signal from a torque sensor 15 on the shaft 6. The resultant time-related characteristics provide an indication of the quality of the sample.

The cylindrical surfaces 2 and 3 of the rotor 4 and stator 5 are ribbed parallel to the rotational axis of the shaft 6 so that the rotational torque measured by the torque sensor 15 is dependent upon the viscosity V of the sample rubber. The load cell 14, on the other hand, responds to the force which acts parallel to the shaft 6 in consequence of the shear brought about in the sample by the rotation; this force is dependent upon the elasticity of recovery E of the sample rubber.

Figure 4:
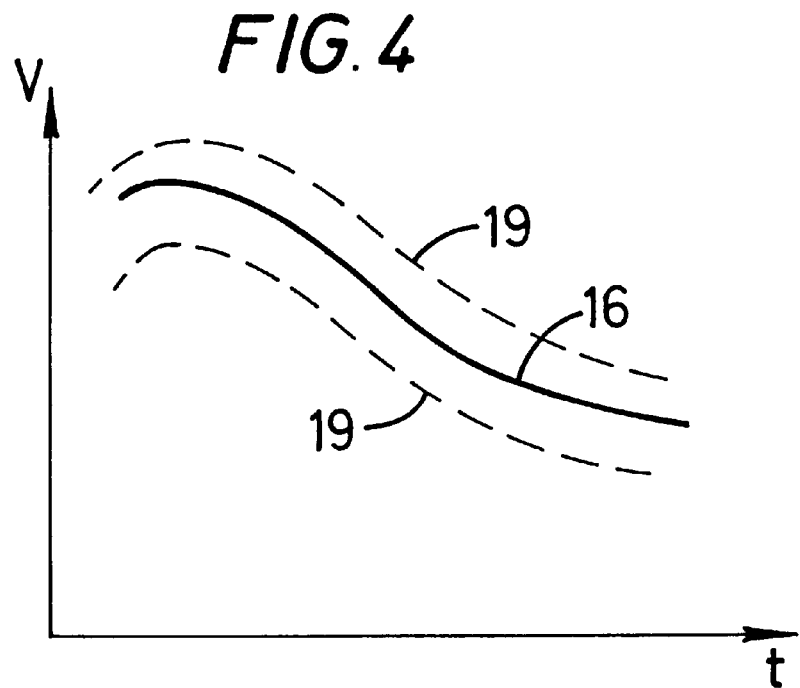
FIGS. 4 and 5 are illustrative of characteristics plotted from measurements taken during operation of the rubber-testing apparatus of FIG. 1.
Figure 5:
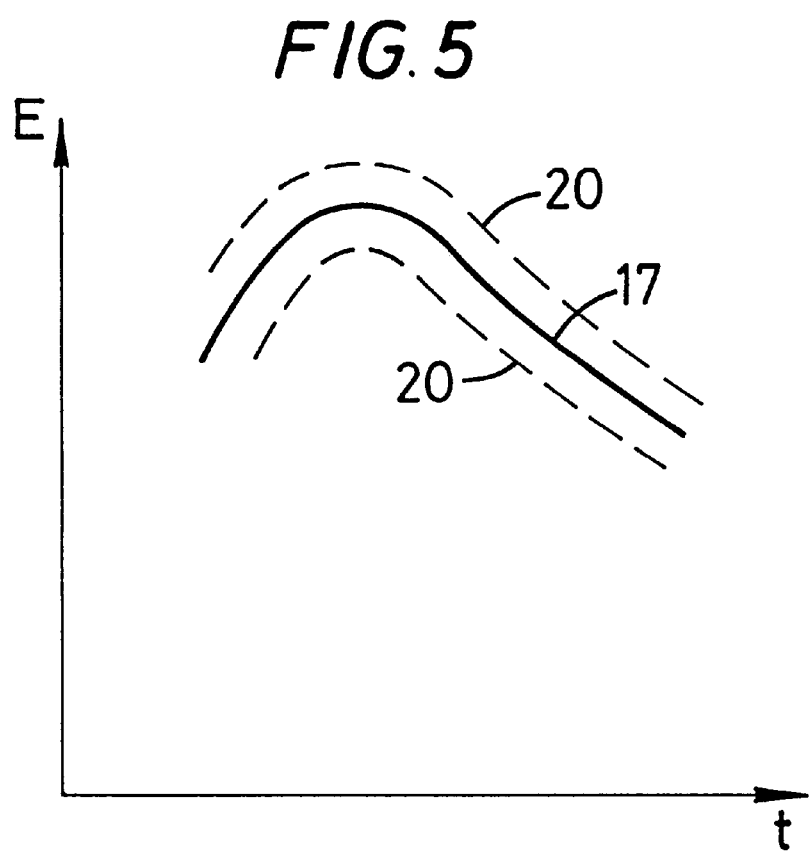

FIGS. 4 and 5 illustrate, respectively, viscosity V and elasticity E characteristics 16 and 17 which have been plotted in accordance with the signals derived from the torque sensor 15 and the load cell 14 during testing of a rubber sample. The sample may be of raw rubber (natural or synthetic) taken from a bale of rubber for the purpose of assessing its quality and therefore acceptability or otherwise for processing. The viscosity and elasticity characteristics are plotted for the sample over a period of some minutes with the temperature of the sample regulated by means of a heater 18 in thermal contact with the stator 5.

More particularly, the heater 18 is regulated to maintain the sample at substantially the same temperature as that of the compounded rubber leaving the masticator-mixer in the primary processing of the rubber. The duration for which the testing apparatus is operated and measurements are taken, is substantially the same as that for which the compounding process is carried out in the masticator-mixer, and the speed of rotation of the shaft 6 is chosen to replicate the highest rate of shear to which the rubber is submitted in the process (for example, $100\ s^{-1}$).

Testing of samples of various supplies of raw rubber is carried out to derive for each an appropriate pair of V and E characteristics. The different rubbers are processed to identify which is the most satisfactory for the application concerned, and from this the corresponding pair of V and E characteristics provides a criterion or standard for acceptance or otherwise of raw rubber for processing. A sample of each new batch of raw rubber is tested and its pair of V and E characteristics compared with the standard pair. If within certain limits there is a match, then the new batch can be accepted for processing with a greater degree of certainty for the maintenance of consistency of resultant product than otherwise would be the case. The tolerance limits applicable are chosen in dependence upon the degree of consistency required and may be plotted on the characteristics as by pairs of lines 19 and 20 shown in FIGS. 4 and 5, to define the range of acceptability.

It is to be recognised that the standard V and E characteristics are in general applicable as appropriate criteria of quality only in regard to the particular manufacturing line and conditions for which they were derived. However, similar V and E characteristics do indicate rubbers of similar quality or processability on the same machines or machines of similar operation (for example shear rate) under similar conditions (for example temperature and duration). Raw-rubber supplies can therefore be characterised by their V and E characteristics for a particular test, and accepted for manufacture if those characteristics are within the appropriate tolerance ranges of the standard characteristics for that manufacturing process.

Although the method of the invention is of especial importance in relation to the testing of raw rubber before processing starts, it may be applied to the rubber during processing. It may be applied to the compounded rubber prior to its submission to the next stage of processing, for example, extrusion, calendering, or injection-moulding. More especially, the sample may be taken from the output of the mastication-mixing stage and in this case the duration of testing, the speed of rotation of the shaft 6, and operation of the heater 18 will be related to the duration, shear conditions (for example, $1,000\ s^{-1}$), and temperature applicable in the next processing stage. The rubber product of this next stage may also be tested in a comparable way in accordance with the conditions applicable to the following stage, so that as processing proceeds, V and E characteristics for each successive stage are plotted and compared with standard V and E characteristics of acceptability derived for that respective stage of the process.

Access to the space 1 can be gained by lifting the chamber 7, and with it the plate 11, clear of the rotor 4 and stator 5, on rods 21. This enables the space 1 to be cleared after testing, but also enables the space 1 to be loaded directly with a strip sample of the rubber bent round to fill the space 1, or with an annular stamping of the sample rubber, if desired.

I claim:

1. In a method of testing rubber in which a sample of the rubber is entered in a space defined between opposed surfaces of two members that are driven for rotation relative to one another, and during this relative rotation measurements are taken of the viscous torque of the sample and the force it exerts along the axis of relative rotation, to provide a measure of quality of the sample, the improvement wherein the opposed surfaces are two cylindrical surfaces that are coaxial with said axis, said cylindrical surfaces defining said space as an annular space, the sample is entered in the annular space to fill it, and the sample is confined to the annular space during the taking of said measurements.

2. A method according to claim 1 wherein a multiplicity of measurements of the viscous torque and the axial force are derived during a period of relative rotation of the two members to provide time-related characteristics dependent respectively upon viscosity and elasticity of recovery of the sample.

3. A method according to claim 2 including a further step for determining whether the rubber is acceptable, said further step including determination of the degree of conformity of said time-related characteristics to predetermined criteria.

4. A method according to claim 2 wherein the temperature of the sample is controlled during said period.

5. A method according to claim 1 wherein the sample is a sample of raw natural or synthetic rubber.

6. A method according to claim 1 wherein the sample is a sample of compounded rubber taken from the product of primary mastication and mixing of raw rubber.

7. A method according to claim 1 wherein the sample is a sample of the product of extrusion, calenderino, or injection-moulding of compounded rubber.

8. A method according to claim 1 wherein said measurements are made for each of a series of samples taken at successive stages of manufacture of a rubber product, for the purpose of control of consistency of such product.

9. A method according to claim 1 wherein the axial length of the annular space is substantially larger than its radial width.

10. A method according to claim 1 wherein the speed of relative rotation of the two members when the measurements are taken lies within the range 50 to 1,000 revolutions per minute.

11. A method according to claim 1 wherein the speed of relative rotation of the two members when the measurements are taken lies within the range 100 to 500 revolutions per minute.

12. Apparatus for testing a sample of rubber, comprising two relatively-rotatable members having opposed surfaces that define a space between the two members for receiving the sample, means for rotating the two members relative to one another, means to derive a measurement dependent upon the viscous torque of the sample, and means to derive a measurement dependent upon the force exerted along the axis of relative rotation of the members during such rotation, wherein said space is an annular space defined between two cylindrical surfaces, the two cylindrical surfaces are coaxial with said axis, and the apparatus also includes means for closing both ends of the annular space for confining the sample thereto.

13. Apparatus according to claim 12 including means for heating the sample within the annular space.

14. Apparatus according to claim 12 wherein the axial length of the annular space is substantially larger than its radial width.

15. Apparatus according to claim 12 including means for selectively blocking one end of the annular space, and wherein said means for deriving a measurement dependent upon axial force is responsive to the force exerted axially by the sample, at the other end of the space.

16. Apparatus according to claim 15 including a loading chamber for receiving the sample of rubber, a plurality of passages coupling the chamber to the annular space, each of said passages opening axially into said one end of said space, ram means for forcing the sample from the loading chamber into the annular space via said passages, and means operable for closing the passages to block said one end selectively.

* * * * *